(12) United States Patent
Rouleau

(10) Patent No.: US 6,419,850 B1
(45) Date of Patent: *Jul. 16, 2002

(54) SYSTEM AND COMPOSITION FOR DECONTAMINATING FLUIDS

(75) Inventor: Henri Rouleau, Nogent sur Marne (FR)

(73) Assignee: Airel-West, Hialeah, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/782,519

(22) Filed: Jan. 10, 1997

Related U.S. Application Data

(63) Continuation of application No. 08/325,785, filed on Oct. 19, 1994, now abandoned, which is a continuation-in-part of application No. 07/893,317, filed on Jun. 3, 1992, now abandoned.

(30) Foreign Application Priority Data

Jun. 3, 1991 (FR) .............................. 91 06636

(51) Int. Cl.⁷ .............................. C02F 1/50; C02F 5/08; A61L 2/18
(52) U.S. Cl. ....................... 252/180; 252/175; 252/181; 422/28; 422/16; 422/17; 106/35
(58) Field of Search ................................ 252/175, 180, 252/181; 422/28, 16, 17; 210/702, 755, 749, 754; 106/35

(56) References Cited

U.S. PATENT DOCUMENTS

| | | | |
|---|---|---|---|
| 3,445,038 A | 5/1969 | Booth et al. | 222/56 |
| 3,655,172 A | 4/1972 | Ingels | 261/138 |
| 4,056,470 A | 11/1977 | Carpenter | 210/94 |
| 4,175,283 A | 11/1979 | Buchwald et al. | 364/153 |
| 4,861,559 A | 8/1989 | Sugisawa et al. | 422/110 |
| 5,095,925 A | 3/1992 | Elledge et al. | 134/61 |
| 5,200,393 A * | 4/1993 | Weiner | 514/3 |
| 5,208,257 A * | 5/1993 | Kabara | 514/552 |
| 5,300,296 A * | 4/1994 | Holly et al. | 424/427 |

OTHER PUBLICATIONS

Le Traitement "Securite" IGN, Airel (month unknown), 1991.*
La Therapeutique De Futur, Airel (month unknown), 1991.*
*The Situation in Dental Operatories*, Airel, 1993.
Le Traitement "Sécurité" IGN, Airel, 1991.
*IGN 500 Traitement De L'Eau Des Sprays Totalement Automatique* Airel, 1992.
*La Therapeutique De Futur*, Airel, 1991.
*How French Dentists Are Using IGN–Calbenium In Their Working Techniques*, Airel, 1993.
*Hackh's Chemical Dictionary*, NcGraw–Hill, Inc., 1969, pp. 92–93.
Kathy Scarbeck, Dental Unit *Water Lines: Curbing infections midstream* AGD Impact, Nov. 1993.
*IGN 500 General Neutralizer Infection* Manual, Airel, 1992.
*The IGN–Calbenium System Fact Sheet*, Airel, 1993.

* cited by examiner

*Primary Examiner*—Alan Diamond
(74) *Attorney, Agent, or Firm*—Gifford, Krass, Groh, Sprinkle, Anderson & Citkowski, P.C.

(57) ABSTRACT

An apparatus and composition of matter for treating tap or distilled water prior to use in irrigation during surgical and medical operations.

7 Claims, 1 Drawing Sheet

SYSTEM AND COMPOSITION FOR DECONTAMINATING FLUIDS

CROSS REFERENCE TO RELATED APPLICATIONS

This is a continuation of application(s) Ser. No. 08/325,785 filed on Oct. 19, 1994 now abandoned, which is a continuation-in-part of U.S. patent application Ser. No. 07/893,317, filed Jun. 3, 1992, now abandoned, entitled SYSTEM FOR DECONTAMINATING FLUIDS.

BACKGROUND OF THE INVENTION

I. Field of the Invention

The present invention relates to the biological decontamination of water used in medical procedures. More particularly, the present invention relates to a system for decontaminating irrigating water used during medical and dental procedures.

II. Description of the Relevant Art

As is well-known, water is commonly used in many medical and dental procedures. However, because of the presence of a variety of biological contaminants, tap or distilled water often requires decontamination prior to use. This is necessary for many reasons, including the prevention of the spread of bacteria and algae, and also to prevent calcification in the fluid circulating system.

In addition, body fluids typically present during dental, medical and surgical procedures are often full of pathogens that, if left viable, contaminate drainage and irrigation systems.

More specifically, in a traditional fluid irrigation system used by doctors and dentists, the fluid, normally water, is easily contaminated by simple contact with the contaminated environment. This is particularly true in dental surgery with the use of the saliva suction pump. The fluid coming from the suction pump is mixed with blood and contaminated saliva which brings with it bacterial pollution. As a result, the surgical tools and tubing become contaminated with a biofilm and algae after a while.

Known methods of decontaminating fluids have failed to overcome these problems. A thorough discussion of the problem is set forth in "Dental Unit Water Lines, Curbing Infections Midstream," in *AGD Impact*, Vol. 21, No. 10 (November 1993).

SUMMARY OF THE PRESENT INVENTION

The present invention discloses a system for treating tap or distilled water prior to use in irrigation during medical and dental procedures. The system comprises an apparatus within which the water is treated and a water treating composition.

This device is designed for dentists, podiatrists, veterinarians, surgeons and other people of the medical field.

Other objects and details of the present invention will become apparent from the following detailed description.

BRIEF DESCRIPTION OF THE DRAWING

The FIGURE illustrates the fluid neutralizing unit of the present invention.

DETAILED DESCRIPTION OF THE PREFERRED EMBODIMENTS OF THE PRESENT INVENTION

Figure 1:
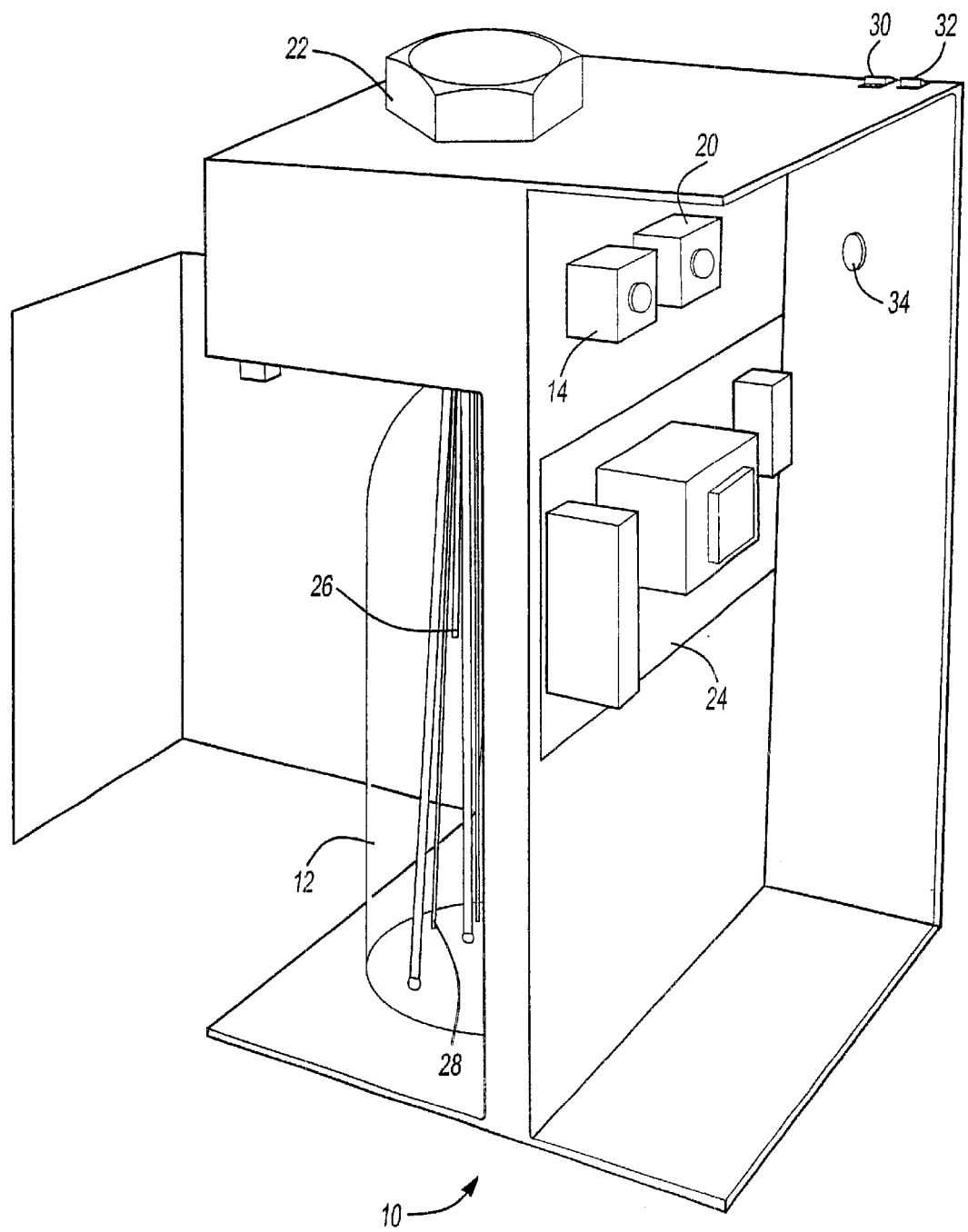

This application claims priority from French Application No. 91 06636, filed Jun. 3, 1991, the entire contents of which are incorporated by reference herein for all purposes.

The present invention concerns a system of decontaminating and treating water used in irrigation during surgery. The present invention permits the use of decontaminated water that has been disinfected and sterilized for various medical procedures. The decontaminated and treated water has cleaning qualities as well as anti-inflammatory, isotonic and hemostatic characteristics. The treated water avoids calcification within the circulating system of the fluid-moving apparatus and also avoids the deposition of algae and contaminated biofilm.

This invention permits the treatment of contaminated water so that the treated water may be used for irrigation during surgery. The system of the present invention comprises both a fluid neutralizing unit and an anti-pathological composition to be introduced into the water supply for use in the neutralizing unit.

The Fluid Neutralizing Unit

The device according to the invention permits a treatment for water which is to be used as a surgical irrigation liquid. The invention operates through a neutralizing unit, generally illustrated as 10, and involves the treatment of water for irrigation in surgery. The unit 10 includes a container 12 of glass, metal or plastic that is filled with water either manually or is joined with a water line to a simple faucet (not shown) or by an electric valve 14. The connection to the general water supply is rigid or is done with a "Staubli®" (trademark) type of fitting or by others. The system to send the water to the unit of irrigation (not shown) is an air elimination process that puts air pressure on the surface of the fluid in the reservoir 12. Pressurization is controlled by an air valve 20, or with a small pump that draws fluid from the reservoir 12. The reservoir 12 is sealed with a closure 22 that allows the introduction of the product for the treatment of the water. An electronic board 24 may control the filling of the container 12 by high and low probes 26, 28. The high probe 26 cuts off the water supply when filling of the reservoir 12 is complete. The low probe 28 is an indicator of the level of the fluid in the reservoir 12 and thus determines the urgency to refill the reservoir 12. A switch 30 allows disengagement by an impulse of the refilling cycle which is controlled by the electronic board 24.

On the electronic board 24 is a buzzer (not shown) which sounds when the low probe 28 is activated. The buzzer will tell the operator how much water remains before the reservoir 12 is empty so that it can be refilled. A general control switch 32 allows electricity to be supplied to the unit 10 and is in series with a fuse 34 which protects the unit 10. The unit 10 can be used all over the world in different voltages.

The Fluid Neutralizing Composition

The fluid neutralizing composition is used in conjunction with the fluid neutralizing unit as described above to treat the water entering the irrigation system. The composition is added as needed to the container 12 of the unit 10. The composition is a mixture of different active ingredients in the form of liquid, powder, or tablets.

The chemical composition is used to stop the calcium and tartar deposits and gives chelating properties to the treated water. The presence of ethylenediaminetetraacetic acid (EDTA) in doses of between 0.2 and 2.0 g per liter gives the water additional complimentary anti-bacterial effects. EDTA is non-toxic for human consumption and the dosage is preferably 1 g, plus or minus 0.5 g per liter of water. The chemical composition has an active antiseptic which is non-toxic for humans. It has anti-bacterial activity as well as anti-viral and anti-algal characteristics. This activity is produced by two products with different target actions. Benzalkonium chloride or a similar compound will act specifically on the membrane lipids, specifically the phospholipidic membranes of bacteria or viruses. The other product, sodium tosylchloramide (or chloramine) or a similar compound will act on the nucleocapsids of the viruses by fixing chloride atoms on them.

The utilization dosage of benzalkonium chloride is 0.12 g plus or minus 0.05 g per liter of water. The utilization dosage of sodium tosylchloramide is 0.02 g plus or minus 0.005 g per liter of water. Benzalkonium chloride or other quaternary ammonium equivalent will give the water cleaning and disinfecting action as well as surface tension modifier properties. This action will be of interest to the dentist for cleaning operation areas, mirrors, drills, and suction pumps. It will improve the qualities of silicone impressions, alginate or hydroalginate molds in the mouth by reducing the surface tension on the cut tooth. A better grip by composites is possible because the treated water more effectively removes etching agents.

A sweetening effect is given by aspartame or a similar compound. A soothing and aromatic effect is given by a natural fragrance stabilized on a powder support base. The composition of the present invention has an anti-inflammatory and healing effect given by allantoin or a similar compound and will enhance the formation of cicatrices. The dosage of allantoin is 0.5 g plus or minus 50% per liter. An isotonic effect will be produced by sorbitol or something similar and will produce a hemostatic and cicatrice-inducing effect in association with EDTA.

The water-treatment composition is composed of the following components:

| | |
|---|---|
| EDTA (ethylenediaminetetraacetic acid) or other derivatives or equivalents | 1.00 g ± 50%; |
| sodium tdsylchloramide or other derivatives or equivalents | 0.02 g ± 50%; |
| benzalkonium chloride or other derivatives or equivalents | 0.12 g ± 50%; |
| aspartame or other sugars | 0.08 g ± 50%; |
| spearmint or other aromas | 0.10 g ± 50%; |
| allantoin or other derivatives or equivalents and | 0.06 g ± 50%; |
| sorbitol or other derivatives or equivalents | 1.12 g ± 50%. |

This formulation is for one dose of 2.5 g for 1 liter of water. In a particular application of the present invention, ice cubes may be added to the fluid in the container 12 and the temperature may be adjusted to approximately 2 degrees celsius for about one hour prior to use in implantology to avoid protein coagulation.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A composition for treating water used in surgery comprising:

0.2 to 2 g ethylenediaminetetraacetic acid (EDTA);

benzalkonium chloride in the amount of 0.12 g, plus or minus 0.05 g; and sodium tosylchloramide in the amount of 0.02 g, plus or minus 0.005 g;

per 1 liter of water.

2. The composition of claim 1 further comprising a compound selected from the group consisting of a sweetener, a flavoring agent, an anti-inflammatory/healing agent, an isotonic agent, and combinations thereof.

3. The composition of claim 2 wherein said sweetener comprises aspartame.

4. The composition of claim 2 wherein said anti-inflammatory/healing agent comprises allantoin.

5. The composition of claim 2 wherein said isotonic agent comprises sorbitol.

6. The composition of claim 2 further comprising EDTA in the amount of 1.00 g, plus or minus 0.5 g, sodium tosylchloramide in the amount of 0.02 g plus or minus 0.004 g, benzalkonium chloride in the amount of 0.12 g plus or minus 0.04 g, aspartame in the amount of 0.08 g plus or minus 0.04 g, flavoring in the amount of 0.10 g plus or minus 0.05 g, allantoin in the amount of 0.06 g plus or minus 0.03 g, and sorbital in the amount of 1.12 g plus or minus 0.56 g per liter of water.

7. A composition for treating water comprising: EDTA in the amount of 1.00 g; plus or minus 0.5 g, sodium tosylchloramide in the amount of 0.02 g plus or minus 0.005 g, benzalkonium chloride in the amount of 0.12 g plus or minus 0.06 g, aspartame in the amount of 0.08 g plus or minus 0.04 g, flavoring in the amount of 0.10 g plus or minus 0.05 g, allantoin in the amount of 0.06 g plus or minus 0.03 g, and sorbital in the amount of 1.12 g plus or minus 0.56 g per liter of water.

* * * * *